(12) United States Patent
Yue

(10) Patent No.: US 10,682,526 B2
(45) Date of Patent: Jun. 16, 2020

(54) DEVICE AND METHOD FOR CONTROLLING ROTATION OF RADIOTHERAPY EQUIPMENT

(71) Applicant: OUR NEW MEDICAL TECHNOLOGIES, Xi'an (CN)

(72) Inventor: Xiaojun Yue, Xi'an (CN)

(73) Assignee: OUR NEW MEDICAL TECHNOLOGIES, Xi'an (CN)

( * ) Notice: Subject to any disclaimer, the term of this patent is extended or adjusted under 35 U.S.C. 154(b) by 233 days.

(21) Appl. No.: 15/961,889

(22) Filed: Apr. 25, 2018

(65) Prior Publication Data

US 2018/0236266 A1 Aug. 23, 2018

Related U.S. Application Data

(63) Continuation of application No. PCT/CN2016/100809, filed on Sep. 26, 2016.

(30) Foreign Application Priority Data

Oct. 26, 2015 (CN) .......................... 2015 1 0702909

(51) Int. Cl.
*A61B 6/00* (2006.01)
*A61N 5/10* (2006.01)
*G05B 19/042* (2006.01)

(52) U.S. Cl.
CPC ......... *A61N 5/1048* (2013.01); *A61N 5/1081* (2013.01); *G05B 19/042* (2013.01);
(Continued)

(58) Field of Classification Search
CPC ......... A61B 5/055; A61B 5/0036; A61B 6/03; A61B 6/032; G01R 33/481
See application file for complete search history.

(56) References Cited

U.S. PATENT DOCUMENTS 7,590,218 B2 9/2009 Scherch et al.
8,242,465 B2 8/2012 Iwata
(Continued)

FOREIGN PATENT DOCUMENTS

CN 1147410 4/1997
CN 1634617 7/2005
(Continued)

*Primary Examiner* — Don K Wong
(74) *Attorney, Agent, or Firm* — Hemisphere Law, PLLC; Zhigang Ma

(57) ABSTRACT

The present disclosure discloses a device for controlling rotation of a radiotherapy equipment, for controlling rotation of at least one rotational load of the radiotherapy equipment about a rotation axis. The device and the radiotherapy equipment form a full-closed-loop structure. The device includes: a detector, configured to detect the rotation of respective rotation axis in real time for each rotational load of the radiotherapy equipment during a treatment process, and record a rotational offset when the rotational load is rotationally deviated; a controller, configured to generate a correction instruction for eliminating the deviation according to the recorded offset when the detector detects at least one of the rotational loads of the radiotherapy equipment is deviated; and a driving apparatus, configured to drive each rotational load of the radiotherapy equipment to rotate about the rotation axis, and drive the deviated rotational load to move according to the correction instruction issued by the controller to eliminate the deviation.

19 Claims, 4 Drawing Sheets

(52) U.S. Cl.
CPC ...... *A61N 5/103* (2013.01); *A61N 2005/1074* (2013.01); *G05B 2219/2652* (2013.01)

(56) References Cited

U.S. PATENT DOCUMENTS

| | | | |
|---|---|---|---|
| 2012/0165651 A1* | 6/2012 | Yamaya | A61N 5/1049 600/411 |
| 2013/0076289 A1 | 3/2013 | Yamaguchi et al. | |
| 2015/0328483 A1 | 11/2015 | Odawara et al. | |
| 2016/0354617 A1 | 12/2016 | Carlsson | |

FOREIGN PATENT DOCUMENTS

| | | |
|---|---|---|
| CN | 101247851 | 8/2008 |
| CN | 102188778 | 9/2011 |
| CN | 102918363 | 2/2013 |
| CN | 202974248 | 6/2013 |
| CN | 103301581 | 9/2013 |
| CN | 103736211 | 4/2014 |
| CN | 104225807 | 12/2014 |
| CN | 105288869 | 2/2016 |
| GB | 2522914 | 12/2015 |
| JP | 2007167411 | 7/2007 |
| JP | 2010246733 | 11/2010 |
| TW | 201433330 | 9/2014 |
| WO | 2015118021 | 8/2015 |

\* cited by examiner

DEVICE AND METHOD FOR CONTROLLING ROTATION OF RADIOTHERAPY EQUIPMENT

This application is a continuation of International Application No. PCT/CN2016/100809, filed on Sep. 29, 2016 and entitled "CONTROL DEVICE AND METHOD FOR ROTATION OF RADIOTHERAPY EQUIPMENT" which claims priority to Chinese Patent Application No. 201510702909.6, filed with the Chinese Patent Office on Oct. 26, 2015 and entitled "CONTROL DEVICE AND METHOD FOR ROTATION OF RADIOTHERAPY EQUIPMENT". The entire disclosures of the prior applications are hereby incorporated by reference in their entirety.

TECHNICAL FIELD

The present disclosure relates to the field of automatic control, and in particular to a device and method for controlling rotation of radiotherapy equipment.

BACKGROUND

For traditional radiotherapy equipment, e.g. head gamma knife, it is usually to control the rotation of a source body and corresponding collimator body therein, by a rotation controller couple thereto, to open and close the radioactive sources. Obviously, the accuracy of synchronous or asynchronous rotation of the source body and the collimator body affects the accuracy of the actual radiation dose emitted to the patient's lesion, further affects the uniformity control of a dose field.

An existing head gamma knife employs a semi-closed-loop feedback detection technology for controlling the synchronous or asynchronous rotation, and the rotation accuracy of the head gamma knife is monitored through encoders self-contained in a servo motor on the loop. However, this detection method cannot accurately reflect the real-time position of the head gamma knife when it rotates, because the motor and the load thereof are composed of a multi-stage transmission chain such as a speed reducer, a gear, etc., and each stage of the transmission mechanism will amplify the rotation error and will eventually reduce the rotation accuracy of the head gamma knife.

SUMMARY

The technical problem to be solved by the present disclosure is to provide a device and method for controlling the rotation of a radiotherapy equipment, which are configured to monitor the actual rotation of a rotational load of the radiotherapy equipment and timely correct an error or deviation occurred, when the rotation of the rotational load is deviated, to improve the safety and positioning accuracy of the radiotherapy equipment.

In order to solve the above technical problems, a technical solution employed by the present disclosure is to provide a device for controlling rotation of a radiotherapy equipment, to control rotation of respective rotational load of the radiotherapy equipment about a rotation axis. The rotation of the rotational load is synchronous rotation or asynchronous rotation, wherein the device and the radiotherapy equipment form a full-closed-loop structure, and the device comprises: a detector, configured to detect the rotation of respective rotation axis in real time for each rotational load of the radiotherapy equipment during a treatment process, and record a rotational offset when the rotational load is rotationally deviated; a controller, configured to generate a correction instruction for eliminating the deviation according to the recorded offset when the detector detects at least one of the rotational loads of the radiotherapy equipment is deviated; and a driving apparatus, configured to drive each rotational load of the radiotherapy equipment to rotate about the rotation axis, and drive the deviated rotational load to move according to the correction instruction issued by the controller to eliminate the deviation.

To solve the above technical problems, another technical solution employed by the present disclosure is to provide a method for controlling rotation of the radiotherapy equipment, to control the rotation of respective rotational load of the radiotherapy equipment about respective rotation axis. The device and the radiotherapy equipment form a full-closed-loop structure. The method comprises: detecting the rotation movement of each rotational load of the radiotherapy equipment in real time during a treatment process; calculating and recording a rotational offset when a deviation occurs at one or more of the rotational loads of the radiotherapy equipment; generating a correction instruction for eliminating the deviation according to the rotational offset; and driving the deviated rotational load to move according to the correction instruction, until the deviation is eliminated.

To solve the above technical problems, another technical solution employed by the present disclosure is to provide a non-transitory computer-readable medium storing computerized code that when executed by an electronic device comprising memory and one or more processors, causes the processor to: detect the rotation movement of each rotational load of a radiotherapy equipment in real time during a treatment process; calculate and record a rotational offset when a deviation occurs at one or more of the rotational loads of the radiotherapy equipment; generate a correction instruction for eliminating the deviation according to the rotational offset; and drive the deviated rotational load to move according to the correction instruction, until the deviation is eliminated.

Different from the other art, the actual position of the rotation of the source body, the switch body, and the collimator body of the radiotherapy equipment is detected in the present disclosure. During the synchronous or asynchronous rotation of the source body, the switch body, and the collimator body, as long as the rotation axis thereof is detected to be deviated, the deviation is timely corrected by monitoring the actual rotation of the rotational loads of the radiotherapy equipment, thereby improving the safety and positioning accuracy of the radiotherapy equipment.

DETAILED DESCRIPTION

The technical solutions of the present disclosure will be further described in detail below in conjunction with specific embodiments. Obviously, the described embodiments are merely a part of the embodiments of the present disclosure, rather than all the embodiments. All other embodiments obtained by a person of ordinary skill in the art based on the embodiments of the present disclosure shall fall within the protection scope of the present disclosure.

Full-closed-loop monitoring systems and semi-closed-loop monitoring systems are common monitoring methods in the field of automatic control. The semi-closed-loop monitoring system monitors the driving link of a final implementing actuator in the entire system, but not monitoring the final implementing actuator. The full-closed-loop monitoring system monitors the final implementing actuator of the entire system and compensate for the errors caused by any link in the system. For radiotherapy equipment, e.g. a gamma head knife, the rotary part thereof is used as the final actuator. The control accuracy of the rotation is closely related to the uniformity of the dose field of the radiotherapy equipment and the accuracy of the actual dose absorbed by the lesion. Therefore, it is preferable to introduce full-closed-loop monitoring system to perform precise control.

Figure 1:
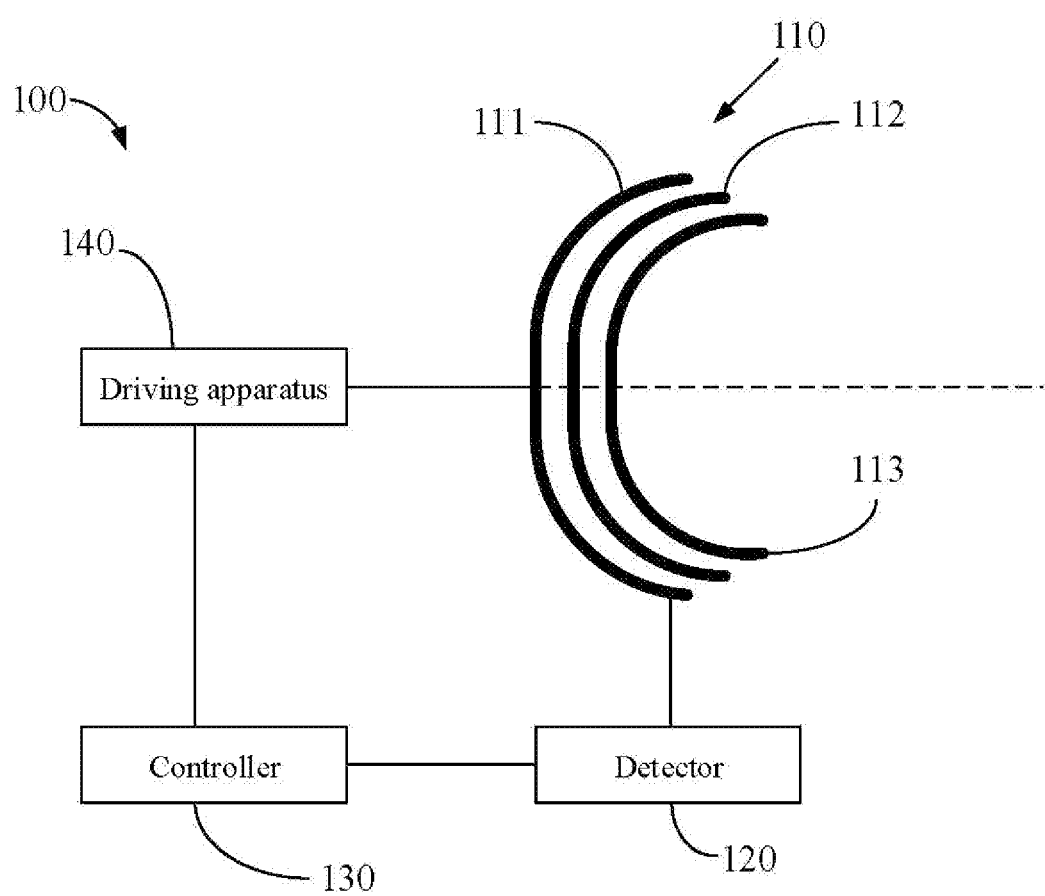
FIG. 1 is a schematic structural diagram of a device for controlling rotation of a radiotherapy equipment, according to a first embodiment of the present disclosure.

Referring to FIG. 1, which is a schematic structural diagram of a first embodiment of a device for controlling rotation of a radiotherapy equipment provided by the present disclosure. The device 100 includes a detector 120, a controller 130, and a driving apparatus 140. Combining with at least one rotational load 110 of the radiotherapy equipment (not shown), a full-closed loop structure is formed.

In at least one embodiment, the rotational loads 110 include, at least, a source body 111, a switch body 112, and a collimator body 113 that are sequentially covered. The source body 111, the switch body 112, and the collimation body 113 are respectively in a bowl-shaped structure, while being rotatable synchronously or asynchronously along an axis perpendicular to the bottom of the bowl structure. Since the source body 111, the switch body 112, and the collimator body 113 are sequentially covered, they are considered to rotate along the same rotation axis. The detector 120 is connected to the rotational loads 110 to monitor, at least, the rotation of the source body 111, the switch body 112, and the collimator body 113. In some embodiments, the detector 120 employs a circular grating for monitoring. When the rotation of any one or more of the source body 111, the switch body 112, and the collimator body 113 is deviated, rotational offset is monitored/detected by the detector 120 immediately. The detector 120 sends the controller 130 the rotational offset of the source body 111, the switch body 112, and the collimator body 113 when occurs. The controller 130 calculates a corrected rotational offset required for normal rotation according to the detected rotational offset, and further sends a correction instruction to the driving apparatus 140. The driving apparatus 140 is configured to drive each component of the rotational loads to rotate in a normal state, and correct the rotation of a deviated component according to the correction instruction, to perform a normal rotation.

For the radiotherapy equipment of the present embodiment, the source body 111 is provided with radioactive material for radiotherapy, and the radiation rays is harmful to the human body. However, by controlling the rotation of the source body 111, the switch body 112, and the collimation body 113 very accurately, effective treatment can be achieved, while reducing harm to the medical staff and the patient's healthy tissue. At first, the controller 130 sets the source body 111, the switch body 112, and the collimator body 113 of the rotational loads to rotate at a certain rate and direction, so that the irradiation of the radioactive rays is emitted to the patient according to the treatment plan. During the treatment process, the detector 120 monitors the rotation status of the source body 111, the switch body 112, and the collimator body 113 in real time, and the extension line along the rotation axis of the source body 111, the switch body 112, and the collimator body 113 is perpendicularly passing through an annular center of the detector 120, in this embodiment. When the rotation of one or more of the source body 111, the collimator 112, and the switch body 113 is deviated, the rotation axis thereof is also deviated relative to original rotation axis with deviation. It should be noted that the deviation according to the present disclosure includes directional deviation and positional deviation. The detector 120 monitors the respective rotational load 110 which is deviated and sends the corresponding rotational offset to the controller 130. The controller 130 sends a correction instruction to the driving apparatus 140, wherein the correction instruction is an instruction to eliminate the deviation, when the rotation of any one or more of the source body 110, the switch body 120, and the collimator 130 is deviated. The driving apparatus 140 drives the corresponding parts to move according to the correction instruction, for eliminating the deviation and recovering a normal rotation.

Different from the other arts, the control device for rotating the radiotherapy equipment of the present disclosure performs actual position monitoring on the rotation of the source body, the collimator, and the switch body. The deviation for the corresponding axis of rotation is detected and the corresponding rotational offset is calculated during the synchronous or asynchronous rotation. As such, by monitoring the actual rotation of the rotating part of the radiotherapy equipment, it is timely corrected when the rotation of any one of the source body, the collimator, and the switch body is deviated, thereby improving the safety and positioning accuracy of the radiotherapy equipment.

Figure 2:
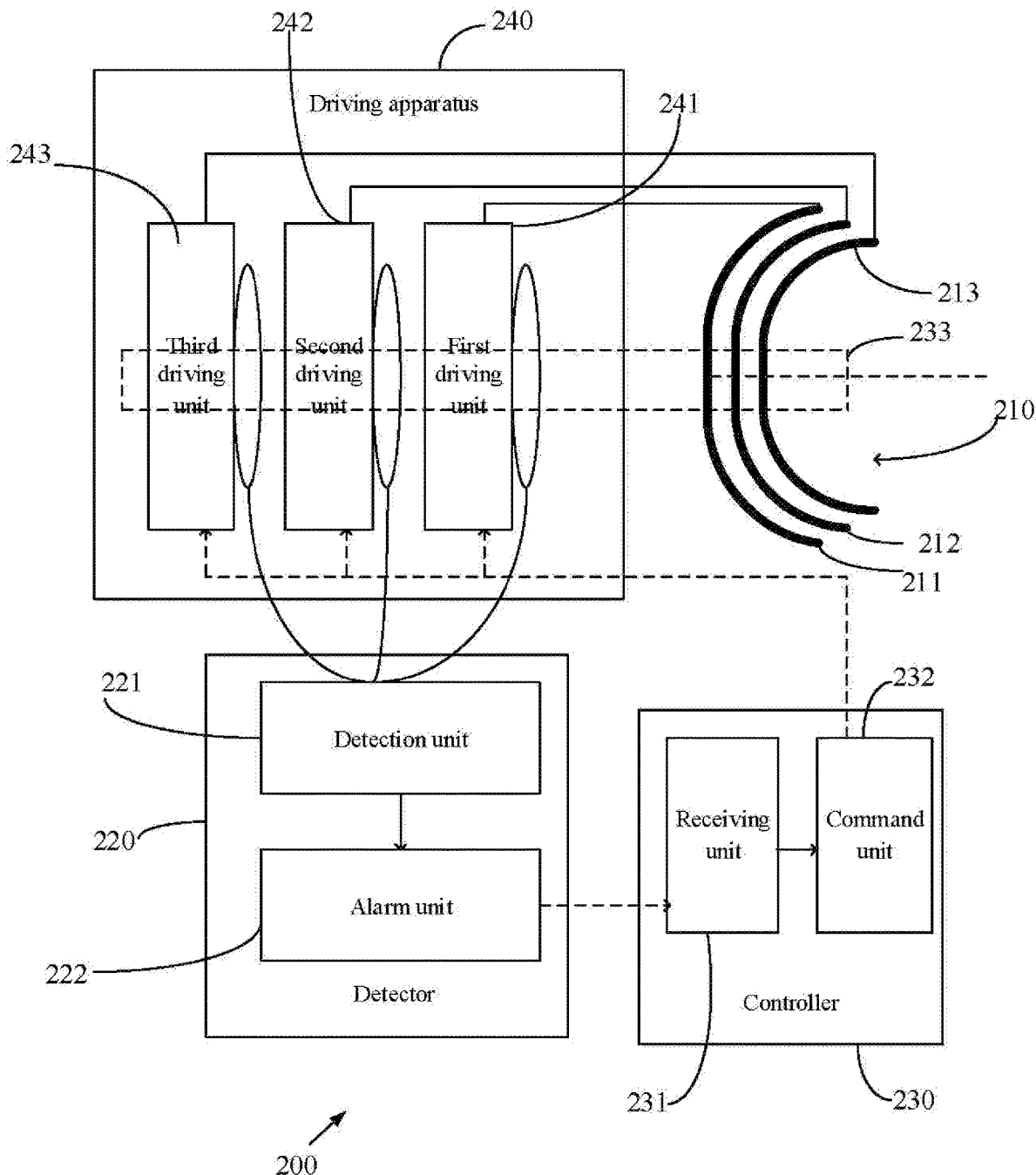
FIG. 2 is a schematic structural diagram of a device for controlling rotation of a radiotherapy equipment, according to a second embodiment of the present disclosure.

Referring to FIG. 2, FIG. 2 is a schematic structural diagram of a second embodiment of a device for controlling rotation of a radiotherapy equipment provided by the present disclosure. The device 200 includes a detector 220, a controller 230, and a driving apparatus 240. Combining with the rotational loads 210, a full-closed loop structure is formed.

In this embodiment, the rotational loads 210 include, at least, a source body 211, a switch body 212, and a collimator body 213 that are sequentially covered. The source body 211, the switch body 212, and the collimation body 213 are respectively in a bowl-shaped structure, while being rotatable synchronously or asynchronously along an axis perpendicular to the bottom of the bowl structure. The source body 211, the switch body 212, and the collimator body 213 are sequentially covered and rotated by using rotation control technique. When in use, the source body 211, the switch body 212, and the collimation body 213 are components of the radiotherapy equipment for directly emitting radiation to treat the patient. Through controlling the relative rotation of the three loads, the source radioactive emission is accurately controlled to be opened or closed, according to a predetermined treatment plan. In opposite, if the relative rotation of the source body 211, the switch body 212, and the collimator body 213 is deviated without control, a medical accident will occur.

The detector 220 is configured to monitor the rotation of the source body 211, the collimator 212, and the switch body 213, including a detection unit 221 and an alarm unit 222. The detection unit 221 of the detector 220 is configured to detect the rotation of the source body 211, the switch body 212, and the collimator body 213 and calculate the rotational offset when deviation is occurred, respectively. In this embodiment, the detection unit 221 detects the position of the rotation axis of the source body 211, the switch body 212, and the collimator body 213. When any one or more of the source body 211, the switch body 212, and the collimation body 213 is deviated, the detection unit 221 of the detector 220 calculates and records the rotational offset. In the present embodiment, the rotational offset referred to herein includes positional offset and angular offset. The positional offset means that the positions of the rotation axis of the source body 211, the switch body 212, and the collimator body 213 is deviated from an initial position of the rotation axis in a parallel direction. The angular offset means that the rotation axis of the source body 211, the switch body 212, and the collimator body 213 no longer perpendicularly passes through the annular surface of the detector 220, but with an angle to the vertical direction. When any one or more of the source body 211, the switch body 212, and the collimator body 213 are deviated while in rotational movement, the alarm unit 222 receives the detected rotational offset, issues an alarm signal, and notifies the controller 230 of the rotational offset. The rotational offset is included in the alarm signal. In the present embodiment, a circular grating is used in the detector, which is capable of accurately calculating and feeding back the rotational offset and digitally control the rotation axis of the source body 211, the switch body 212, and the collimator body 213, so that the actual position of the axis is strictly controlled at any time, ensuring the rotation of the source body 211, the switch body 212, and the collimator body 213 having high dynamic accuracy and steady-state. As mentioned above, when the source body 211, the switch body 212, or the collimator body 213 is deviated, the rotational offset thereof is accurately detected and calculated by the circular grating and the controller 230 is notified of the subsequent correction.

In this embodiment, before performing the detection by the detector 220, the controller 230 sets a virtual rotation axis 233 parallel or being overlapping to the rotation axis of the source body 211, the switch body 212, and the collimator body 213. The virtual rotation axis 233 is virtual and cannot be observed by human eyes, and the position of the virtual rotation axis 233 is fixed. This is a pre-correction step before using the corrected method mentioned above.

The controller 230 includes a receiving unit 231 and a command unit 232. The receiving unit 231 of the controller 230 receives the alarm signal and obtains the rotational offset according to the alarm signal. The command unit 232 generates a correction instruction according to the offset. The correction instruction is generated according to the rotational offset included in the alarm signal. The correction instruction includes the correction offset needed to resume the normal rotation according to the calculated rotational offset of the one or more rotational loads 210, which is calculated by the controller 230. After the correction instruction is generated, the command module 232 transmits the correction instruction to the driving apparatus 240.

The driving apparatus 240 includes a first driving unit 241, a second driving unit 242, and a third driving unit 243. The first driving unit 241, the second driving unit 242, and the third driving unit 243 respectively drive the source body 211 and the switch body 212 and the collimator body 213 to rotate. The driving apparatus 240 is powered by a power source (not shown). Upon receiving the correction instruction transmitted by the command unit 232, the first driving unit 241, the second driving unit 242, and the third driving unit 243 simultaneously parse the correction instruction to obtain the correction offset of the corresponding source body 211, the switch body 212, and the collimator body 213. And, the deviation is eliminated according to the correction offset in the correction instruction, and the normal rotation is resumed.

Further, the detector 220 is respectively disposed inside the first driving unit 241, the second driving unit 242, and the third driving unit 243. In this embodiment, the detector 220 includes the circular grating, and the circular grating is a ring-shaped structure. The rotation axis of the source body 211, the switch body 212, and the collimator body 213 are perpendicular to the circular surface of the ring structure, and are perpendicular to the center of the ring structure. When each of the circular gratings (e.g. the detector 220) detects that the rotation of the source body 211, the switch body 212, and the collimator body 213 of the radiotherapy equipment is deviated, an alarm signal is sent to the controller 230 so that the controller 230 obtains the rotational offset according to the detector 220. The rotational offset which is used to recover the normal rotation movement of the deviated rotational loads, is calculated by the corresponding drive unit in the driving apparatus 240.

Different from the other arts, the control device for rotating the radiotherapy equipment of the present disclosure performs actual position monitoring or detection on the rotation of the source body 211, the switch body 212, and the collimator body 213 thereof. The deviation for the corresponding rotation axis is detected during the synchronous or asynchronous rotation. As such, by monitoring or detecting the actual rotation of the rotational loads of the radiotherapy equipment, it is timely corrected when the rotation of any one or more of the source body, the collimator, and the switch body is deviated, thereby improving the safety and positioning accuracy of the radiotherapy equipment.

Figure 3:
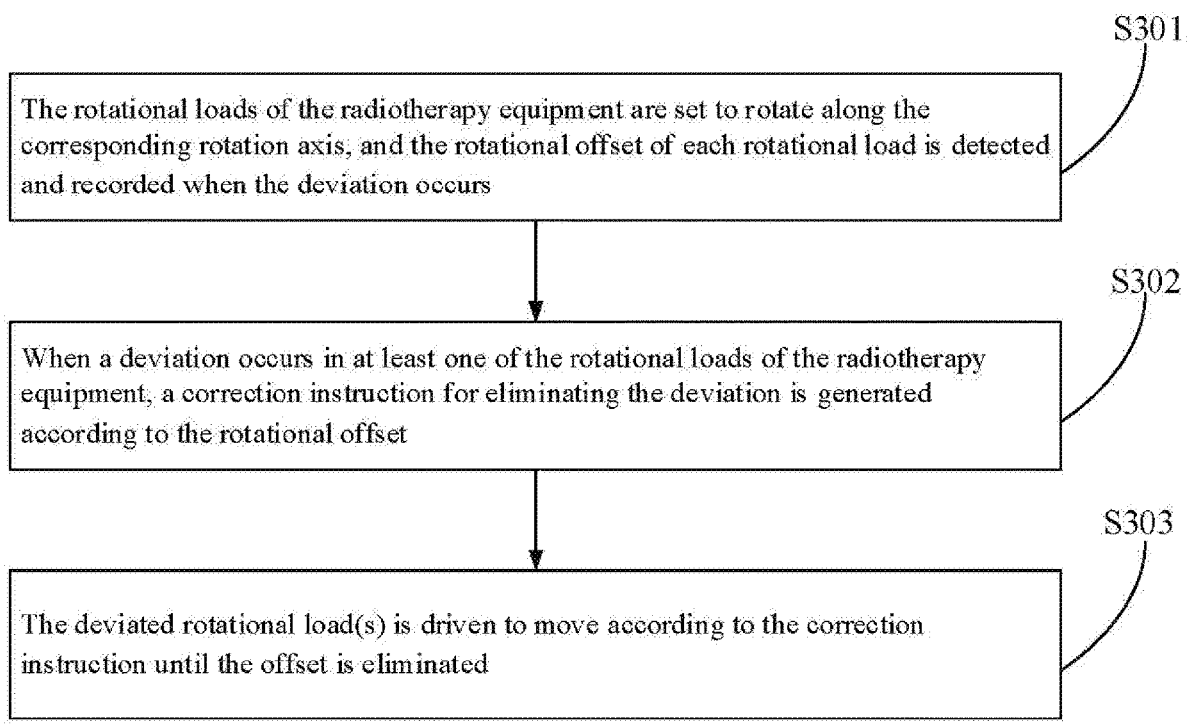
FIG. 3 is a schematic flowchart of a method for controlling rotation of a radiotherapy equipment, according to a first embodiment of the present disclosure.

Referring to FIG. 3, FIG. 3 is a schematic flowchart of a first embodiment of a method for controlling rotation of a radiotherapy equipment according to the present disclosure. The method includes steps of S301 to S303, exemplarily.

In step S301, the rotational loads of the radiotherapy equipment are set to rotate along the corresponding rotation axis, and the rotational offset of each rotational load is detected and recorded when the deviation occurs.

During a normal operation of the radiotherapy equipment, the source body, the switch body and the collimator body are in a bowl-shaped structure, and are sequentially covered and controlled by different driving motors. The three are rotatable along an axis passing vertically through the bottom of each bowl structure while allowing relative rotation therebetween. Only by accurate controlling of the rotation of the source body, the switch body, and the collimator body, effective treatment is performed. In the present disclosure, it is possible to accurately control the radioactive source to be opened or closed in the radiotherapy equipment according to a predetermined treatment plan, reducing harm to the medical personnel and the healthy tissue of the patient.

During the operation of the source body, the switch body, and the collimator body, rotation of the three is monitored or detected by a circular grating, and the circular grating is a ring structure. Since the source body, the switch body, and the collimator body are sequentially covered, in an ideal state, the rotation axis along which the respective rotations coincide on the same straight line. The straight line is set to be perpendicular to the circular surface of the circular grating ring structure and passes through the center of the circle surface.

In step S302, when a deviation occurs in at least one of the rotational loads of the radiotherapy equipment, a correction instruction for eliminating the deviation is generated according to the rotational offset.

In this step, the position of the circular grating is fixed, and when the rotation, e.g. position of the rotation axis of the source body, the switch body and the collimator body and are detected to be deviated from that of the circular grating, for example, the straight line of the rotation axis of the source body, the switch body or the collimator body is no longer perpendicular to the circular surface of the annular structure of the circular grating, or the straight line is not perpendicularly passing through to the center of the circular surface, it is determined that the rotation of the source body, the switch body, or the collimator body is deviated, from normal operation and needed to be corrected. After the rotational offset is calculated by the circular grating, a correction instruction is generated according to the offset. The correction instruction is an instruction to eliminate the deviation and includes a correction procedure determined by comparing a first offset between the to-be-corrected, axis and that of the circular grating, to a second offset between a preset rotation axis and that of the circular grating. After the correction instruction is sent, the process proceeds to step S303.

In step S303, the deviated rotational load(s) is driven to move according to the correction instruction until the offset is eliminated.

In this step, after the correction instruction is issued, the driving motor that drives the source body, the switch body, and the collimator body rotates to eliminate deviation that occurs during the rotation of the source body, the switch body, and the collimator body according to the correction offset in the correction instruction, resuming the work of the radiotherapy equipment back to normal.

Different from the other art, the actual position of the rotation of the source body, the switch body, and the collimator body of the radiotherapy equipment is detected in the present disclosure. During the synchronous or asynchronous rotation of the source body, if the switch body, and the collimator body, the rotation axis thereof is detected to be deviated, the deviation is timely corrected by monitoring or detecting the actual rotation of the rotational loads of the radiotherapy equipment, thereby improving the safety and positioning accuracy of the radiotherapy equipment.

Figure 4:
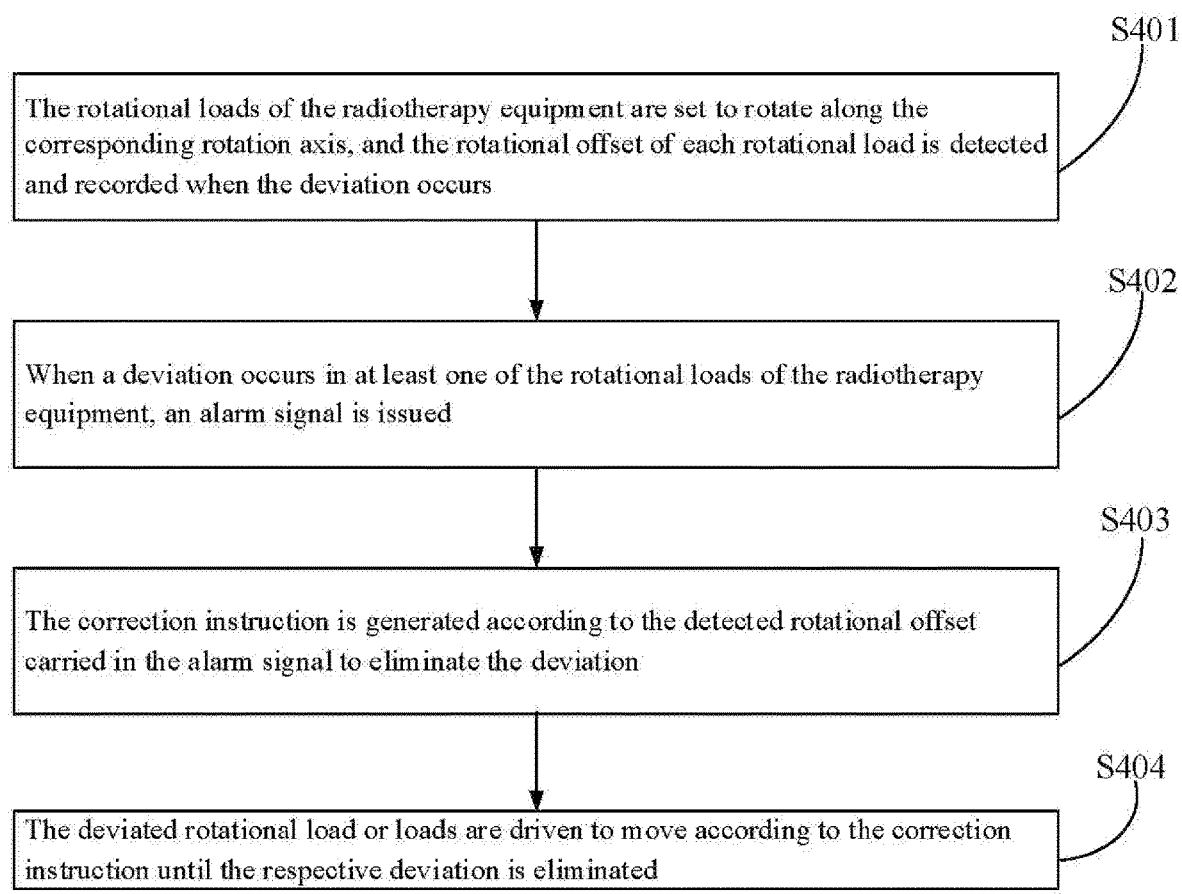
FIG. 4 is a schematic flowchart of a method for controlling rotation of a radiotherapy equipment, according to a second embodiment of the present disclosure.

Referring to FIG. 4, FIG. 4 is a schematic flowchart of a second embodiment of a method for controlling rotation of a radiotherapy equipment provided by the present disclosure. The method includes steps of S401 to S404.

In step S401, the rotational loads of the radiotherapy equipment are set to rotate along the corresponding rotation axis, and the rotational offset of each rotational load is detected and recorded when the deviation occurs.

This step is same as the previous embodiment of FIG. 3 and will not be described again. Similarly, after the radiotherapy equipment enters operation, the process proceeds to step S402.

In step S402, when a deviation occurs in at least one of the rotational loads of the radiotherapy equipment, an alarm signal is issued.

Similar to the previous embodiment, a circular grating is used to monitor the rotation of the source body, the switch body, and the collimator body of the radiotherapy equipment. In this embodiment, the circular grating monitors the relative position of the virtual rotation axis to that of the rotation axis along which the source body, the switch body, and the collimator body rotate. And when the rotation axis of the source body, the switch body, and the collimator body deviates, the position or angle of the rotation axis thereof with respect to the circular grating is changed. Therefore, it is possible to detect the deviation by using the circular grating. After the deviation is determined, the circular grating determines the type of the deviation and calculates the value of the rotational offset, and sends the alarm signal to the controller. The process continues to step S403.

In step S403, the correction instruction is generated according to the detected rotational offset carried in the alarm signal to eliminate the deviation.

In this step, alarm signal is parsed after being received. The rotational offset carried therein is obtained, and the correction instruction is generated based on the rotational offset. The correction instruction is an instruction for eliminating the deviation for any one or more of the source body, the switch body, and the collimator body, and includes a correction offset required for restoring the normal rotation. The correction offset is added to the correction instruction and the correction instruction is sent to a driving motor.

In step S404, the deviated rotational load or loads are driven to move according to the correction instruction until the respective deviation is eliminated.

In this step, after the correction instruction is issued, the driving motor that drives the source body, the switch body, and the collimator body rotates to eliminate the deviation that occurs during the rotation of the source body, the switch body, and the collimator body, according to the correction offset carried in the correction instruction, resuming the work of the radiotherapy equipment back to normal. In some embodiments, a non-transitory computer-readable medium storing computerized code that when executed by an electronic device comprising memory and one or more processors, is provided to the radiotherapy equipment, to cause the processor to complete the method for controlling rotation of a radiotherapy equipment, as mentioned above.

A person of ordinary skill in the art may understand that all or some of the processes in the methods of the foregoing embodiments may be implemented by a computer program instructing relevant hardware. The program may be stored in a computer readable storage medium. The program corresponding to the device for controlling rotation of a radiotherapy equipment shown in FIG. 1 and FIG. 2 may be stored in the readable storage medium, and is executed by at least one processor, to implement the foregoing methods for controlling rotation of a radiotherapy equipment. The methods include the processes in the method embodiments in FIG. 3 to FIG. 4. The storage medium may be a magnetic disk, an optical disc, a read-only memory (ROM), a random access memory (RAM), or the like. In some embodiments, the storage medium includes a non-transitory storage medium.

For example, in this disclosure, an electronic device for controlling rotation of a radiotherapy equipment is provided, to control rotation of respective rotational load of the radiotherapy equipment about respective rotation axis. The device includes memory and one or more processors. The processor (or also referred to as a central processing unit (CPU)) is the computing core and the control core of the device. The processor may parse various types of instructions in the terminal and process various types of data of the device, for example, read a computer readable instruction stored in the memory to perform the method steps provided in the embodiments shown in the foregoing FIG. 3 to FIG. 4. The memory (such as a memory) is a volatile or non-volatile computer readable storage medium, is a storage device of the device, and is configured to store a computer readable instruction such as a program and data. The memory herein may include a built-in memory of the device, and may certainly further includes an expanded memory supported by the device. The memory provides storage space. The storage space stores an operating system of the device. The operating system may include, but not limited to, a Windows system (an operating system), an Android system (a mobile operating system), an iOS system (a mobile operating system), and the like.

In this embodiment, the processor is configured to access the at least one memory and operate according to the computer program code, to execute the following steps: detecting the rotation movement of each rotational load of the radiotherapy equipment in real time during a treatment process; calculating and recording a rotational offset when a deviation occurs at one or more of the rotational loads of the radiotherapy equipment; generating a correction instruction for eliminating the deviation according to the rotational offset; and driving the deviated rotational load to move according to the correction instruction, until the deviation is eliminated.

Different from the other art, the actual position of the rotation of the source body, the switch body, and the collimator body of the radiotherapy equipment is detected in the present disclosure. During the synchronous or asynchronous rotation of the source body, if any one or more of the switch body, and the collimator body, the rotation axis thereof are detected to be deviated, the deviation is timely corrected by monitoring the actual rotation of the rotational loads of the radiotherapy equipment, thereby improving the safety and positioning accuracy of the radiotherapy equipment.

The foregoing descriptions are merely embodiments of the present disclosure, and do not limit the scope of the present disclosure. Any equivalent structure or equivalent process transformation using the description of the present disclosure and the accompanying drawings are directly or indirectly applied to other related technologies shall fall within the protection scope of the present disclosure.

What is claimed is:

1. A device for controlling rotation of a radiotherapy equipment, to control rotation of respective rotational load of the radiotherapy equipment about respective rotation axis, wherein the device and the radiotherapy equipment form a full-closed-loop structure, and the device comprises:
   a detector, configured to detect the rotation of respective rotation axis in real time for each rotational load of the radiotherapy equipment during a treatment process, and record a rotational offset when at least one of the rotational loads are rotationally deviated;
   a controller, configured to generate a correction instruction for eliminating the deviation according to the recorded rotational offset when the detector detects at least one of the rotational loads of the radiotherapy equipment is deviated; and
   a driving apparatus, configured to drive each rotational load of the radiotherapy equipment to rotate about the rotation axis, and drive the deviated rotational load to move according to the correction instruction issued by the controller to eliminate the deviation.

2. The device according to claim 1, wherein the detector comprises a detection unit and an alarm unit, the detection unit is configured to detect the rotation of the rotational load and calculate the rotational offset when deviation is occurred; the alarm unit is configured to issue an alarm signal according to the rotational offset.

3. The device according to claim 2, wherein the controller comprises a receiving unit and a command unit, the receiving unit is configured to receive the alarm signal sent by the detector; and the command unit is configured to generate a correction instruction to send to the driving apparatus according to the alarm signal.

4. The device according to claim 3, wherein the rotational offset is a positional offset or an angular offset, the rotational offset is included in the alarm signal; the correction instruction includes a correction offset calculated by the controller, according to the rotational offset, to resume the deviated rotational load to a normal position.

5. The device according to claim 4, wherein the rotational load of the radiotherapy equipment comprises a source body, a switch body, and a collimator body, and the driving apparatus includes at least one first driving unit, a second driving unit and a third driving unit configured to respectively drive the source body, the switch body and the collimator body to perform synchronous or asynchronous rotation, and eliminate the deviation according to the correction instruction when any one or more of the rotation axis of the source body, the switch body, and the collimator is deviated.

6. The device according to claim 5, wherein the detector is one or more circular grating which is respectively disposed in the first driving unit, the second driving unit and the third driving unit.

7. The device according to claim 1, wherein the controller is configured to further control the axis of the rotational load to be parallel to or overlapped with a preset virtual rotation axis.

8. A method for controlling rotation of a radiotherapy equipment, to control the rotation of respective rotational load of the radiotherapy equipment about respective rotation axis, wherein the device and the radiotherapy equipment form a full-closed-loop structure, and the method comprises:
   detecting the rotation movement of each rotational load of the radiotherapy equipment in real time during a treatment process;
   calculating and recording a rotational offset when a deviation occurs at one or more of the rotational loads of the radiotherapy equipment;
   generating a correction instruction for eliminating the deviation according to the rotational offset; and
   driving the deviated rotational load to move according to the correction instruction, until the deviation is eliminated.

9. The method according to claim 8, wherein the generating the correction instruction for eliminating the deviation according to the rotational offset comprises:
   sending an alarm signal according to the rotational offset when it is detected that at least one of the rotational loads of the radiotherapy equipment is deviated;
   generating the correction instruction based on the rotational offset included in the alarm signal, wherein the correction instruction is used to calculate a correction offset in which the deviated rotational load returns to normal rotation.

10. The method according to claim 8, wherein the rotational offset of the rotation axis comprises a positional offset or/and an angular offset.

11. The method according to claim 10, further comprising:
   providing at least one circular gratings to respectively detect the rotation of the rotational load of the radiotherapy equipment; and when at least one of rotational load is deviated, determining the type of the rotational offset and calculating the value of the rotational offset.

12. The method according to claim 8, wherein the rotation of the at least one rotational load is synchronous rotation or asynchronous rotation.

13. The method according to claim 8, wherein before detecting and recording the rotational offset of each rotational load, the method further comprises:

controlling the rotation axis of the rotational load to be parallel to or overlapped with a preset virtual rotation axis.

14. A non-transitory computer-readable medium storing computerized code that when executed by an electronic device comprising memory and one or more processors, causes the processor to:

detect the rotation movement of each rotational load of a radiotherapy equipment in real time during a treatment process;

calculate and record a rotational offset when a deviation occurs at one or more of the rotational loads of the radiotherapy equipment;

generate a correction instruction for eliminating the deviation according to the rotational offset; and drive the deviated rotational load to move according to the correction instruction, until the deviation is eliminated.

15. The non-transitory computer-readable medium according to claim 14, wherein the computerized code further causes the processor to:

send an alarm signal to a controller according to the rotational offset when it is detected that at least one of the rotational loads of the radiotherapy equipment is deviated;

generate, by the controller, the correction instruction based on the rotational offset included in the alarm signal, wherein the correction instruction is used to calculate a correction offset in which the deviated rotational load returns to normal rotation.

16. The non-transitory computer-readable medium according to claim 14, wherein the rotational offset comprises a positional offset or/and an angular offset.

17. The non-transitory computer-readable medium according to claim 16, wherein the rotational loads of the radiotherapy equipment comprise a source body, a switch body, and a collimator body, and the computerized code further causes the processor to:

provide three circular gratings to detect the rotation of the source body, the switch body, and the collimator body of the radiotherapy equipment, respectively; and when at least one of the source body, the switch body, and the collimator body is deviated, determine the type of the rotational offset and calculate the value of the rotational offset.

18. The non-transitory computer-readable medium according to claim 14, wherein the rotation of the at least one rotational load is synchronous rotation or asynchronous rotation.

19. The non-transitory computer-readable medium according to claim 14, wherein the computerized code further causes the processor to:

before detecting and recording the rotational offset of each rotational load, control each rotation axis of the rotational loads to be parallel to or overlapped with a preset virtual rotation axis.

\* \* \* \* \*